United States Patent [19]

Bailey

[11] Plant 4,837

[45] Apr. 13, 1982

[54] NORWAY MAPLE—POND CULTIVAR

[75] Inventor: Rodney P. Bailey, St. Paul, Minn.

[73] Assignee: Bailey Nurseries, Inc., St. Paul, Minn.

[21] Appl. No.: 123,774

[22] Filed: Feb. 22, 1980

[51] Int. Cl.[3] ..... A01H 5/12

[52] U.S. Cl. ..... Plt./51

[58] Field of Search ..... Plt./51

*Primary Examiner*—Robert E. Bagwill

*Attorney, Agent, or Firm*—Burns, Doane, Swecker & Mathis

[57] ABSTRACT

A new and distinct variety of Norway Maple, botanically known as *Acer platanoides* is provided. The new variety is distinguished from the regular Norway Maple by a marked tendency to branch at an early stage of development and a more vigorous growth habit. Also, the leaves of the new variety are darker green in color, and less pronounced lenticels are exhibited.

6 Drawing Figures

SUMMARY OF THE INVENTION

The new and distinct variety of Norway Maple was discovered by me during 1974 while growing in a large cultivated block of several thousand regular Norway Maple tree seedlings (non-patented) growing at the Hageman farm of Bailey Nurseries, Inc. in the south half of the SE ¼ of Section 13, Township 27, Range 21 at Cottage Grove, Minn. Immediately prior to this discovery the trees of the block had been transplanted from a similar block which was begun by the planting of regular Norway Maple seed during 1972 at property of the Bailey Nurseries, Inc. located at Hastings, Minn.

At the time of my discovery my attention was attracted to a single plant in the seedling block which was significantly different in appearance from all other plants in the block primarily because of its branching growth characteristic, greater height, and greater trunk diameter. Steps were taken to continue to observe this unusual seedling. The plant was first asexually reproduced at my direction during 1977 when budwood was taken which was shipped to the Yamhill, Oreg. property of Bailey Nurseries, Inc. where it was budded onto regular Norway Maple understock. The original tree of the new variety was destroyed during 1977 following the removal of a large quantity of budwood, and accordingly is not presently available. This and subsequent asexual reproduction by budding has confirmed that the distinctive characteristics of the new variety come true to form and are established and transmitted through succeeding propagations.

This new variety of Norway Maple has been named the Pond Cultivar.

BRIEF DESCRIPTION OF THE PHOTOGRAPHS

The trees illustrated are whips which in FIGS. 1 and 2 were propagated by budding at Yamhill, Oreg. during August, 1978 and shipped to Cottage Grove, Minn. following one year's growth where they were photographed while in a dormant stage of development during January, 1980. The color is depicted as nearly true as possible to make the same in a color illustration of this character.

FIG. 1 illustrates a portion of a whip of the Pond Cultivar on the right and a portion of a whip of a regular Norway Maple (non-patented) on the left for comparative purposes. The branching characteristic and the larger trunk diameter of the new variety is apparent.

FIG. 2 illustrates in an enlarged manner a portion of a whip of the Pond Cultivar on the right and a portion of a whip of the regular Norway Maple (non-patented) on the left for comparative purposes. In addition to the branching and larger trunk diameter propensity the new variety exhibits a lighter overall bark appearance with more pronounced lighter bark striations on the older wood, as well as less pronounced lenticels.

FIG. 3 illustrates a two year old tree of the Pond Cultivar growing at Yamhill, Oreg. during September, 1980. This photograph illustrates the highly branched growth habit of the tree which is approximately fourteen feet in height and 1¼ inches in trunk diameter. The lower branches of the tree illustrated have been removed.

FIG. 4 illustrates both surfaces of typical newly formed leaves of the Pond Cultivar. The leaves were photographed on May 27, 1981 and were obtained from a two year old tree growing at Yamhill, Oreg.

FIG. 5 illustrates the typical appearance of newly formed branches or twigs of the Pond Cultivar, the regular Norway Maple, the Superform Maple, and the Emerald Queen Maple. The photograph was taken on May 27, 1981 with the branches or twigs having been obtained from trees growing at Yamhill, Oreg. The lenticels of the new variety are considerably darker in coloration on such newly formed growth.

FIG. 6 illustrates for comparative purposes newly formed leaves of the Pond Cultivar and of the regular Norway Maple. The photograph was taken on May 27, 1981 with the leaves having been obtained from trees growing at Yamhill, Oreg. Later in the growing season as the leaves of the Pond Cultivar mature they will assume a darker green appearance than those of the regular Norway Maple.

DETAILED DESCRIPTION OF THE NEW VARIETY

Unless otherwise stated the new variety has characteristics substantially identical to those of the regular Norway Maple (non-patented). Color terminology used herein is to be accorded its usual dictionary significance.

Figure 1:
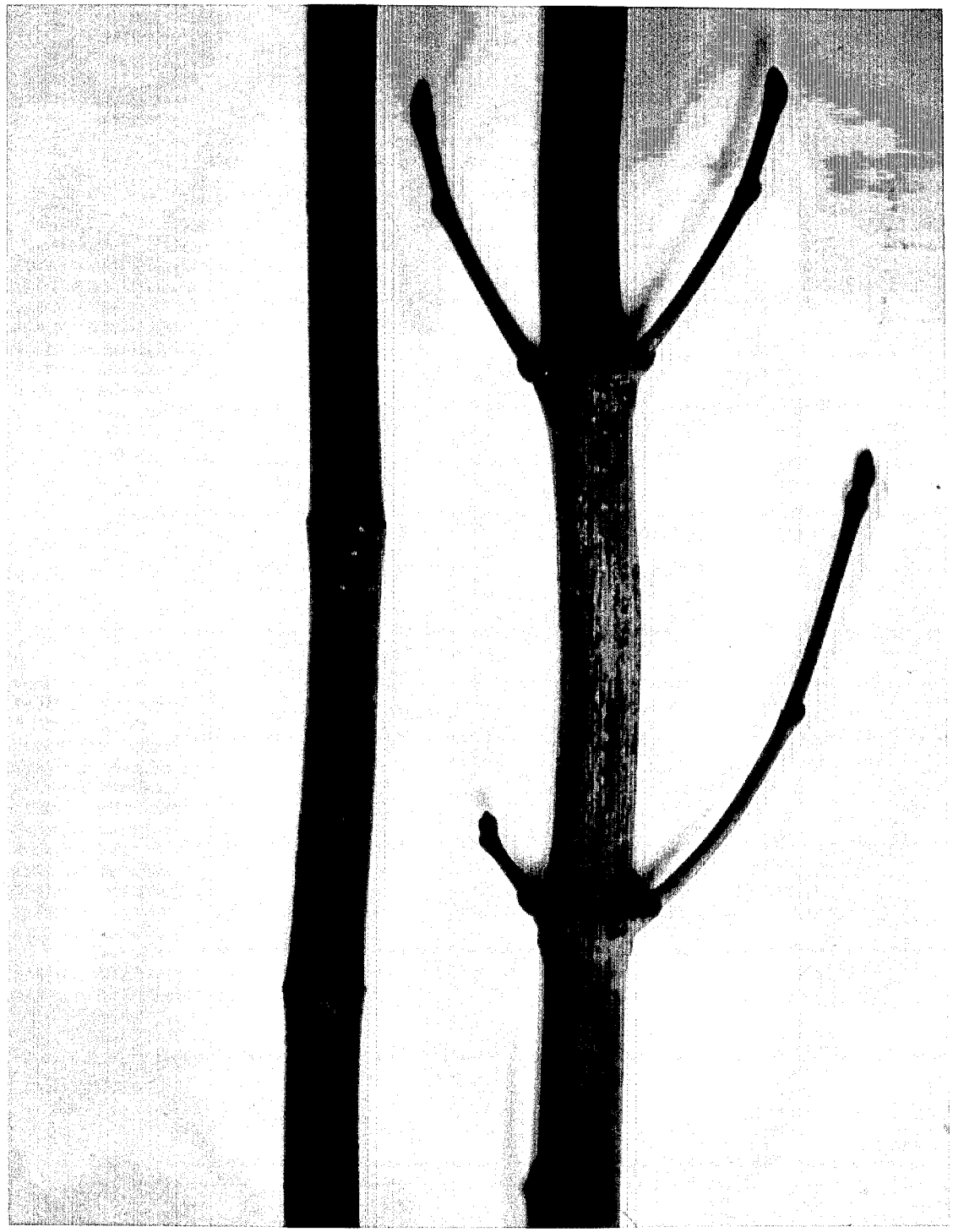
Figure 2:
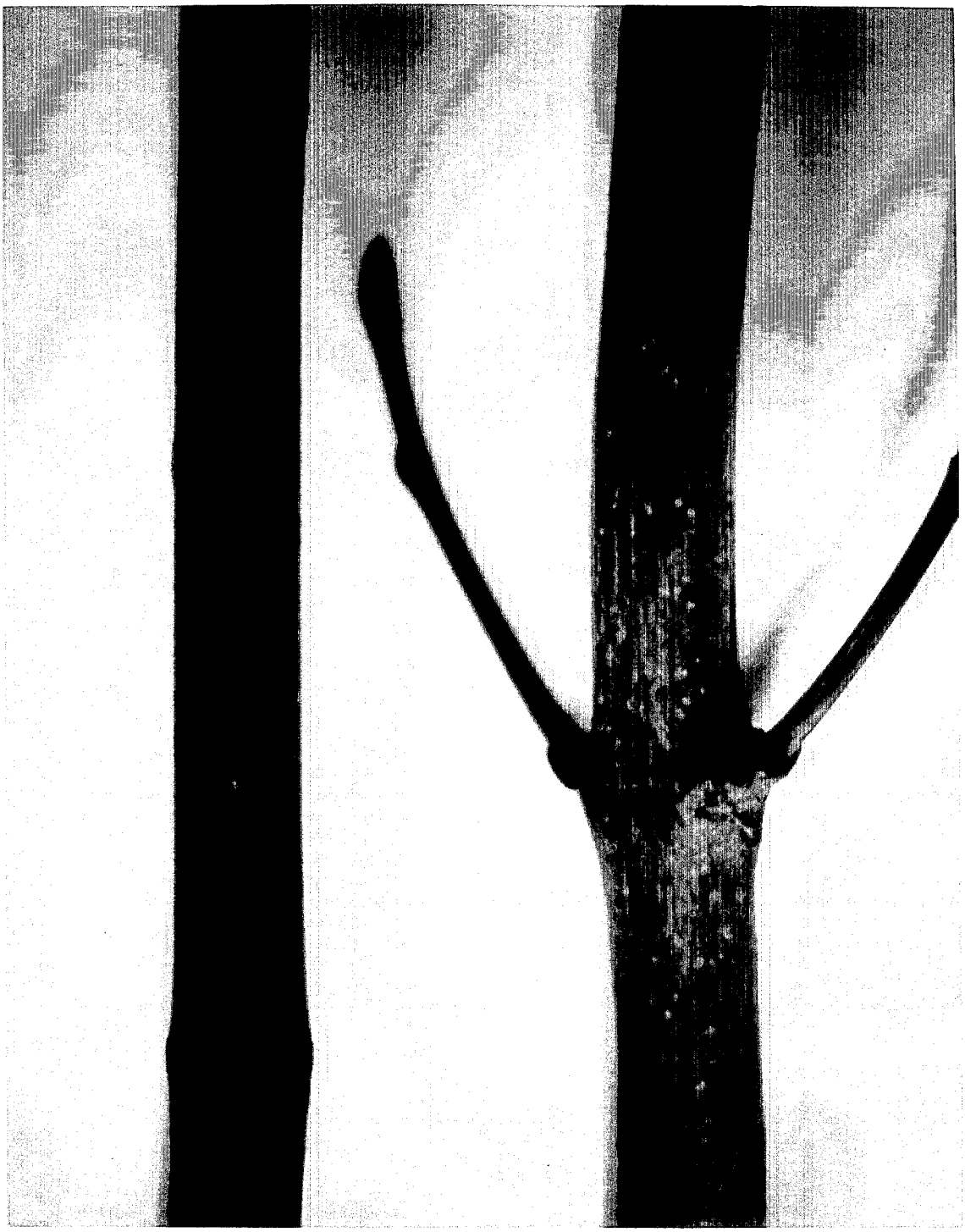

The branching propensity of the new variety is particularly evident at an early age. One year old whips of the new variety exhibit substantial branching as illustrated in FIGS. 1 and 2. On the contrary one year old whips of the regular Norway Maple, as well as of other varieties of *Acer platanoides*, such as Royal Red, Emerald Queen, etc., commonly exhibit no or at most very infrequent branching. See, for instance, the branchless regular Norway Maple whips shown in FIGS. 1 and 2.

The new variety also exhibits an increased vigor at an early age which is manifest by an increased height and trunk diameter when compared to other varieties of *Acer platanoides*. Average heights of one year old whips of representative varieties of *Acer platanoides* grown at Yamhill, Oreg. are set forth below:

| Variety | Average Height in Feet |
|---|---|
| Pond Cultivar | 8.2 |
| Emerald Queen | 7.6 |
| Schwedler | 7.0 |
| Superform | 6.9 |
| Royal Red | 6.3 |
| Crimson King | 5.6 |
| Regular Norway | 5.3 |

Figure 3:
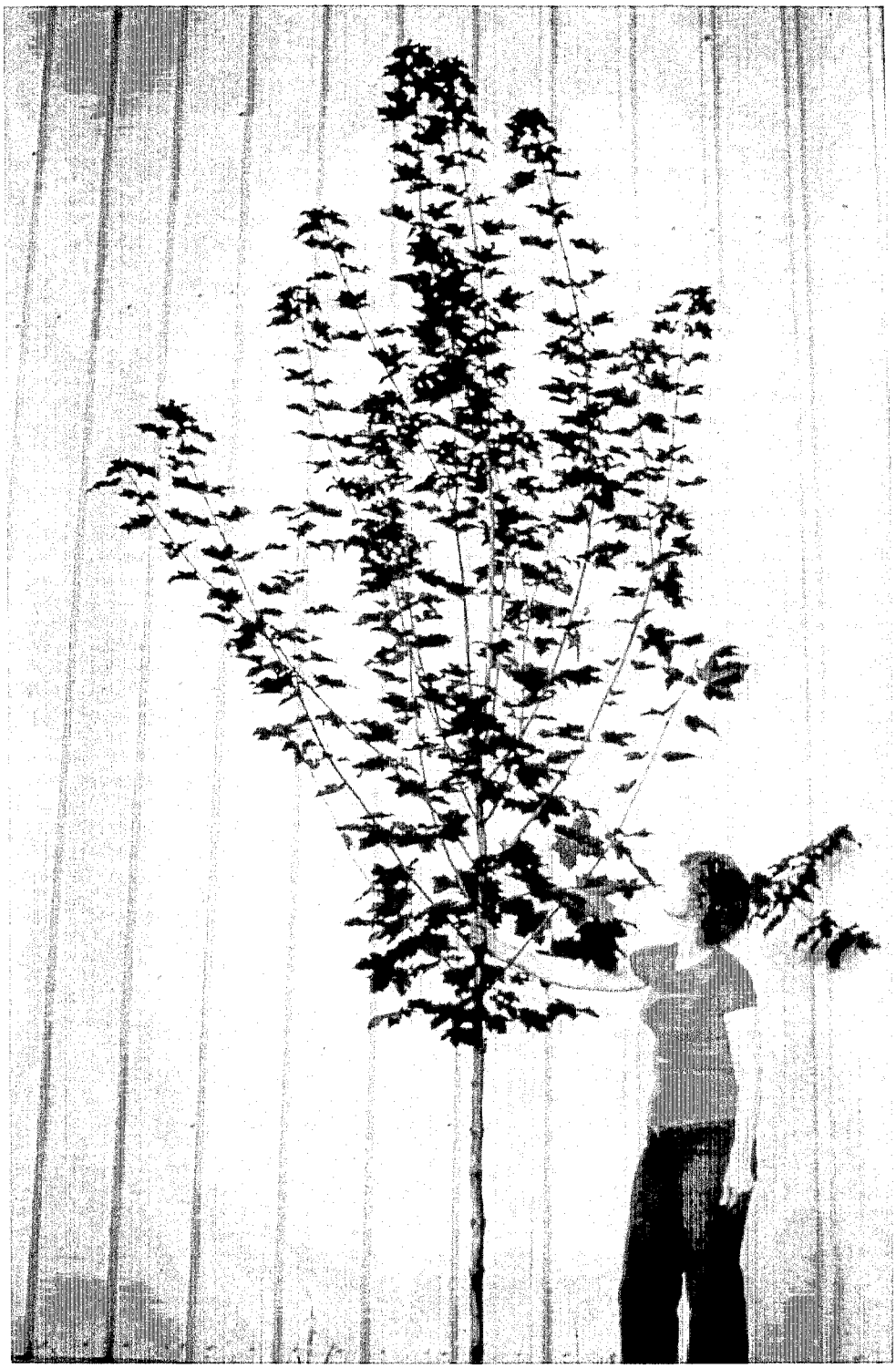

Accordingly, the new variety following one year's growth will average a substantially larger grade size than the regular Norway Maple. Such larger grade size continues to be observed during subsequent years (e.g., for two year old trees). Also, as illustrated in FIGS. 1 and 2, one year old whips of the new variety will exhibit an increased trunk diameter when compared to that of the regular Norway Maple at approximately the same distance above ground level. See the two year old tree of FIG. 3 which is approximately fourteen feet in height and has a trunk diameter of approximately $1\frac{1}{4}$ inches.

Figure 4:
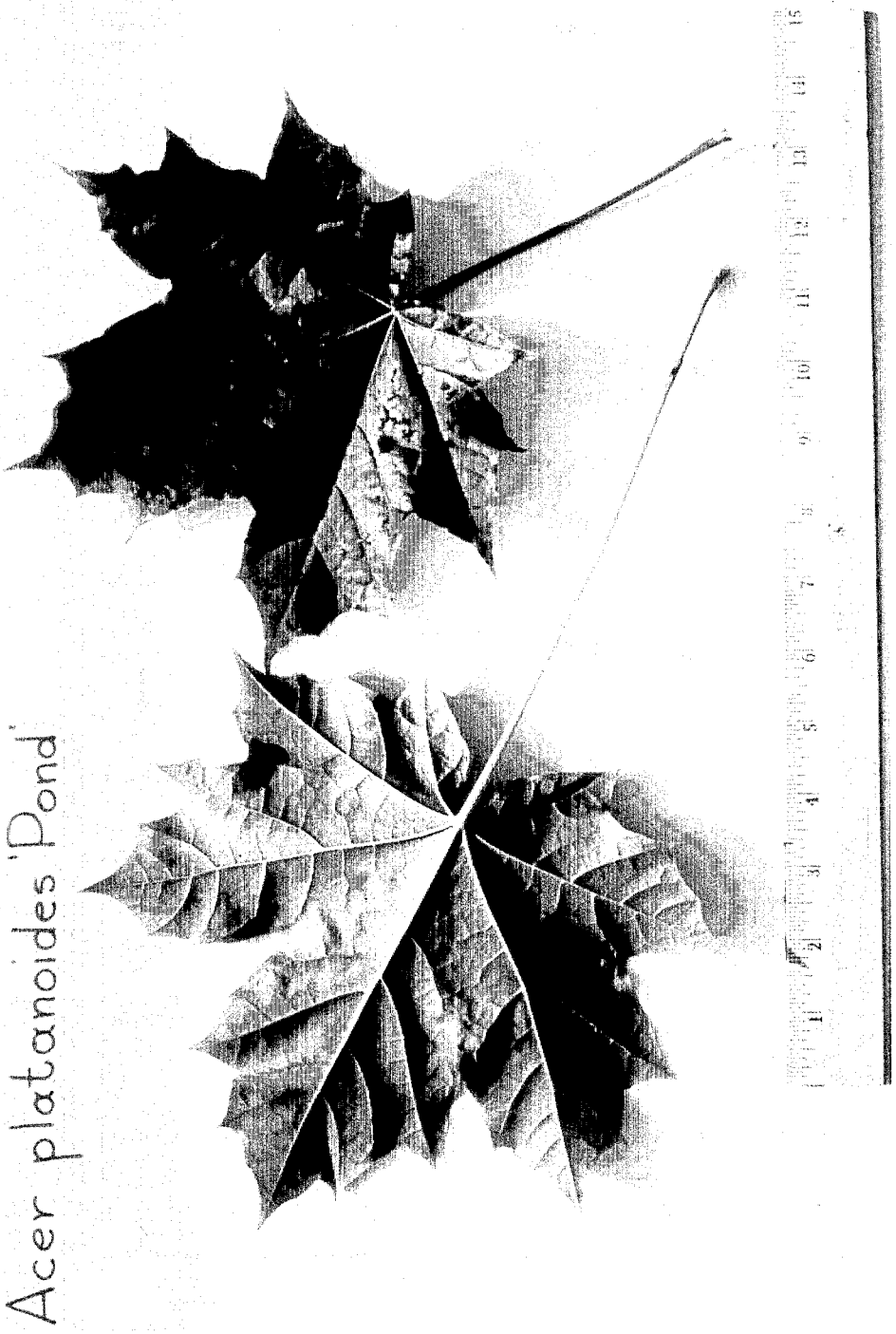
Figure 6:
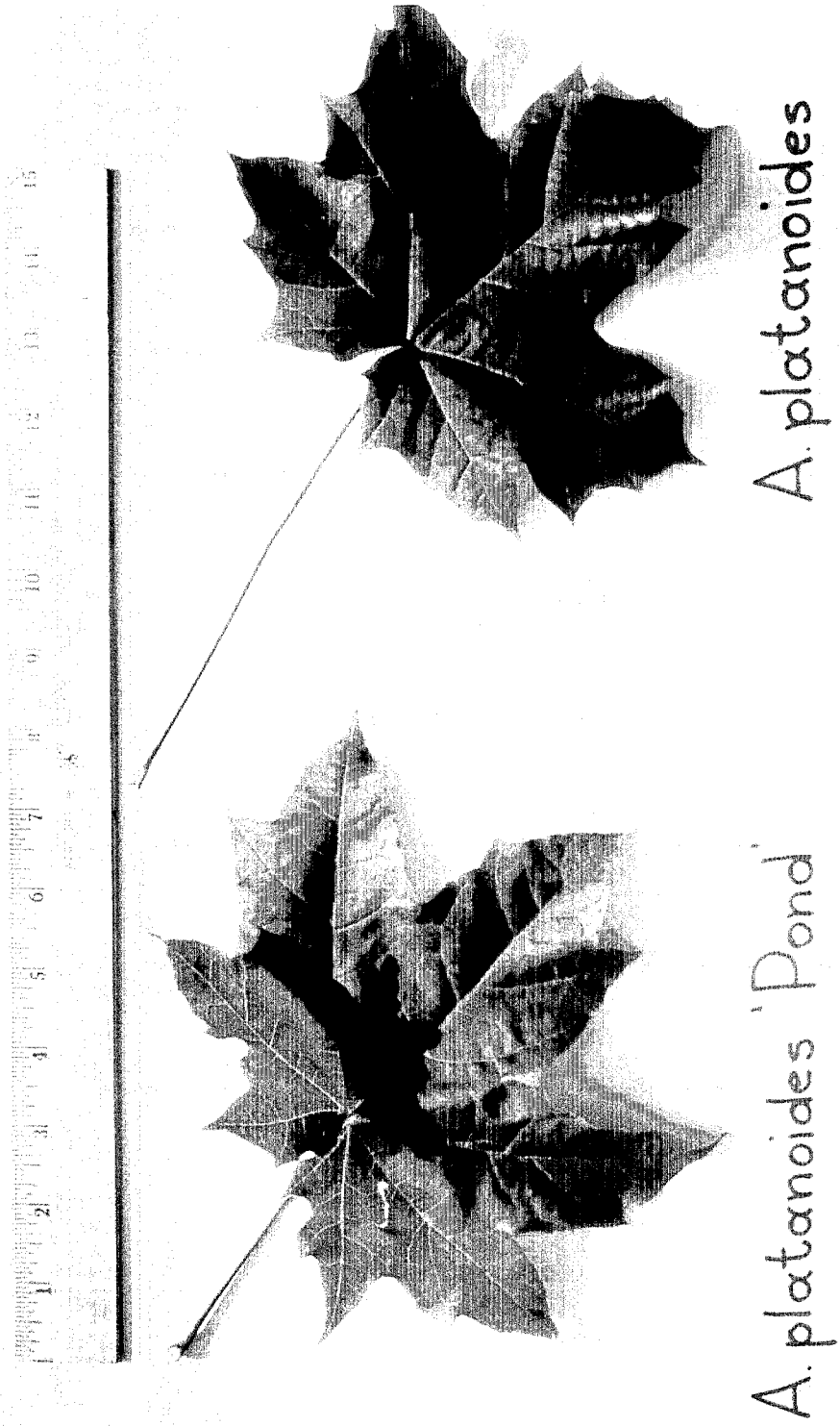

The leaves of the new variety are of a darker green coloration than those of the regular Norway Maple and additionally commonly exhibit a tinge of redness. Such darker coloration is particularly observable when the leaves are fully mature during the latter part of the growing season. The coloration of leaves present on two year old trees of the new variety growing at Yamhill, Oreg. on May 27, 1981 in accordance with the R.H.S. Colour Chart of the Royal Horticultural Society (London) was Yellow-Green Group 147A on the upper surface and Yellow-Green Group 147B on the under surface. See the leaves of FIGS. 4 and 6. Additionally, the leaves of the new variety commonly are cupped slightly forward when viewed from the obverse side particularly during the early part of the growing season. This can be contrasted to the relatively flat leaves of the regular Norway Maple. The coloration of leaf petioles of two year old trees of the new variety growing at Yamhill, Oreg. on May 27, 1981 in accordance with the R.H.S. Colour Chart was Red-Purple Group 184B.

Figure 5:
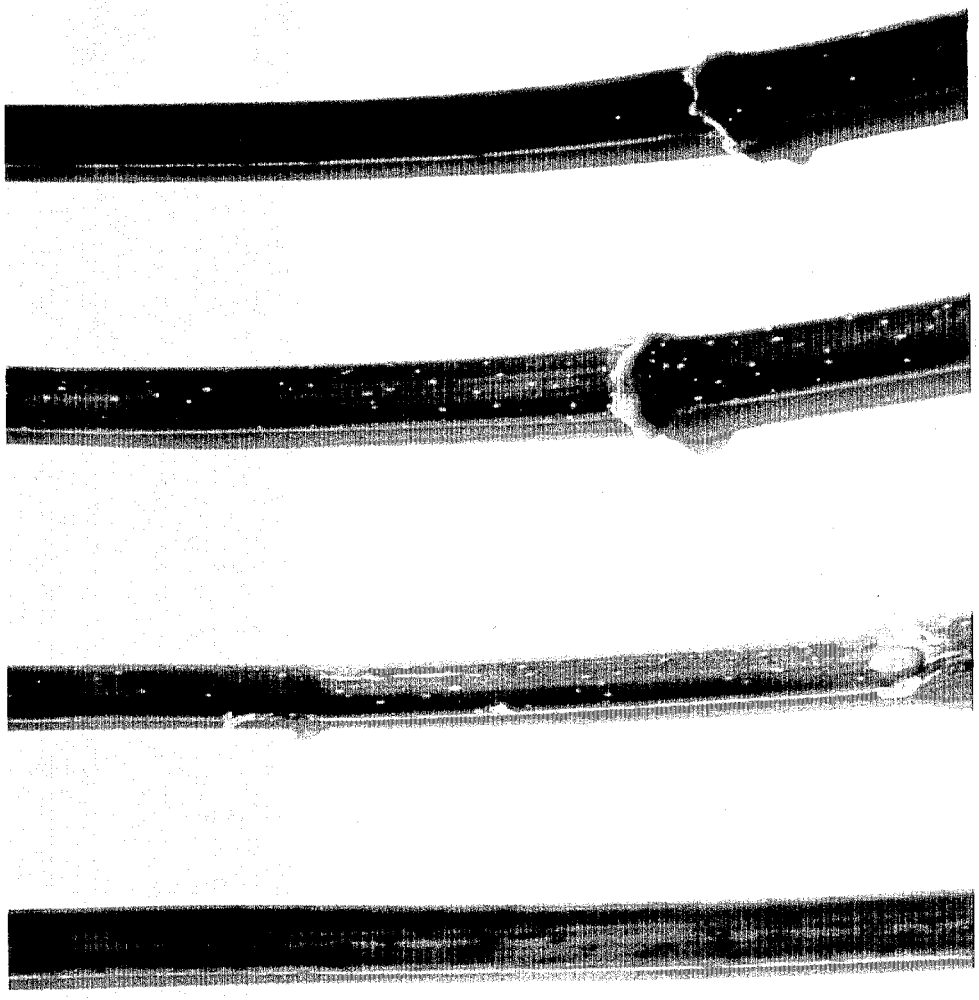

The newly formed branches or twigs of the present variety possess dark lenticels. The coloration of such lenticels present on two year old trees of the new variety growing at Yamhill, Oreg. on May 27, 1981 in accordance with the R.H.S. Colour Chart is Greyed-Purple Group 184A. As seen in FIG. 5 such lenticels are considerably darker than those of the regular Norway Maple, the Superform Maple and the Emerald Queen Maple under the same growing conditions. However, as the branches or twigs mature the lenticels becomes light in color and are less pronounced.

The trunks of one year old whips of the new variety bear less pronounced lenticels when compared to the regular Norway Maple as illustrated in FIGS. 1 and 2.

The newly formed trunk of the new variety commonly is darker in appearance than that of the regular Norway Maple, but upon maturation as illustrated in FIGS. 1 and 2 commonly is lighter in coloration. Also, upon maturation lighter and more pronounced bark striations commonly are visible upon the trunk of the new variety as illustrated in FIGS. 1 and 2. The general coloration of the trunk bark of two year old trees of the new variety growing at Yamhill, Oreg. on May 27, 1981 in accordance with the R.H.S. Colour Chart was Greyed-Green Group 197B, and the coloration of the lighter bark striations was Greyed-Yellow Group 161C.

The dormant buds of the new variety tend to be darker in coloration and slightly smaller than those of the regular Norway Maple. Also, the dormant buds present on one year old whips of the new variety tend to be disposed at an angle so that the distal ends thereof are substantially more removed from the trunk when compared to the bud angle of the regular Norway Maple. Axillary buds commonly are present on one year old whips of the new variety. To date no seed has been observed on the trees of the present variety; however, it is assumed that seed will form upon mature trees of the present variety.

Since fully mature trees of the new variety are not yet available a comparison of mature trees has not been possible. However, the foregoing description will enable one skilled in the identification of the various varieties of *Acer platanoides* readily to distinguish the new variety on the basis of its distinctive characteristics which are apparent at an early age.

I claim:

1. A new and distinct variety of *Acer platanoides*, substantially as illustrated and described, characterized by its general similarity to the common *Acer platanoides*, but being distinct therefrom by (1) a marked propensity to branch at an early age, (2) an increased vigor which is manifest by an increased height and trunk diameter during the first year following budding, (3) the formation of darker green leaves having a tinge of redness which commonly are slightly cupped in configuration, and (4) the exhibition of less pronounced lenticels.

* * * * *

Norway Maple
Regular

Norway Maple
Pond Cultivar

Norway Maple
Regular

Norway Maple
Pond Cultivar

Emerald Queen Maple

Superform Maple

Norway Maple Regular

Norway Maple Pond Cultivar

Norway Maple
Pond Cultivar

Norway Maple
Regular